United States Patent [19]
Jain et al.

[11] Patent Number: 5,337,757
[45] Date of Patent: * Aug. 16, 1994

[54] DEVICE FOR INDUCING AND REGISTERING IMBALANCE

[75] Inventors: Sanjeev Jain, Columbia; John E. Vermette, Baltimore, both of Md.; Richard Weber, Middlesex, N.J.; Robert J. Doub, Baltimore, Md.; Gad Alon, Rockville, Md.; Alan G. Day, III, Timonium, Md.

[73] Assignee: Baltimore Therapeutic Equipment Co., Hanover, Md.

[ * ] Notice: The portion of the term of this patent subsequent to May 11, 2010 has been disclaimed.

[21] Appl. No.: 19,643

[22] Filed: Feb. 18, 1993

Related U.S. Application Data
[63] Continuation of Ser. No. 658,334.

[51] Int. Cl.$^5$ .............................................. A61B 5/103
[52] U.S. Cl. .................................... 128/779; 128/782; 434/258
[58] Field of Search ............... 128/779, 782, 774, 687, 128/695, 696, 700; 434/258; 364/413.01, 413.02

[56] References Cited
U.S. PATENT DOCUMENTS

| | | | |
|---|---|---|---|
| 3,974,491 | 8/1976 | Sipe | 128/779 |
| 4,195,643 | 4/1980 | Pratt, Jr. | 128/779 |
| 4,416,293 | 11/1983 | Anderson et al. | 128/782 |
| 4,426,884 | 1/1984 | Polchaninoff | 73/172 |
| 4,503,705 | 3/1985 | Polchaninoff | 73/172 |
| 4,738,269 | 4/1988 | Nashner | 128/782 |
| 4,813,436 | 3/1989 | Au | 128/779 |
| 4,830,024 | 5/1989 | Nashner et al. | 128/787 |
| 5,042,504 | 8/1991 | Huberti | 128/779 |
| 5,052,406 | 10/1991 | Nashner | 128/782 |

Primary Examiner—Stephen C. Pellegrino
Assistant Examiner—Guy V. Tucker
Attorney, Agent, or Firm—James J. Brown

[57] ABSTRACT

A device is provided for registering and recording induced imbalance in a human subject. A horizontal platform is adapted for controlled, linear displacement in a horizontal plane to induce imbalance. Imbalance and response can be detected and recorded by means of electric contact shoes or other means.

4 Claims, 9 Drawing Sheets

DEVICE FOR INDUCING AND REGISTERING IMBALANCE

This is a continuation of application Ser. No. 07/658,334, filed Feb. 20, 1991, now U.S. Pat. No. 5,209,240.

SUMMARY OF THE INVENTION

The present invention is directed to a system for quantitatively registering and evaluating the response of a human subject to induced imbalance. Additionally, the invention provides a system for re-educating balance reaction, recovery time and motor control in human subjects in which these functions may have become impaired.

BACKGROUND OF THE INVENTION

Many traumatic or disease related musculoskeletal and neurological disorders present, among other signs, deficiencies in equilibrium and righting reactions, as well as inadequate total body and/or segmental sensory-motor control. Orthopedic rehabilitation following trauma, corrective surgery or limb amputation have traditionally recognized that regaining muscle strength and endurance without proper balance responses does not constitute optimal recovery of functions. The recurrent falls of elderly subjects is well documented, including resulting injuries, suffering and high cost. Balance reaction has been one of the recognized factors contributing to such falls.

Numerous neurological disorders including Parkinsonism, cerebral vascular accident (CVA), head trauma, Multiple Sclerosis (MS) and Cerebral Palsy (CP) may not only severely affect standing balance, but profoundly interfere with equilibrium response in sitting, quadruped and even recumbent posture. Clinicians routinely estimate the severity of balance dysfunction and provide various treatment techniques to improve the patient's balance control in all the aforementioned postures.

Traditionally, balance and motor control improvement or lack of it has only been estimated through visual observation of the patient performance.. Whereas such methods are readily available, they are subjective, inconsistent and can detect only very marked changes in balance responses. Without a precise, sensitive and reliable testing method, treatment procedures to improve balance deficiencies are much less effective and efficient than is desirable.

There is, accordingly, a clear need for a system which can overcome these clinical disadvantages by quantitatively documenting objectively, accurately and reliably in a very short time the deficiencies of balance responses and motor control functions of various body postures of human subjects. Further, there is a need for a system which can be programmed to train the subject to overcome postural and neuromuscular disturbances by gradually increasing the demand for balance response, motor control and recovery time in various postures and directions, with accompanying facility in re-testing the patient's progress during each session or as needed.

DESCRIPTION OF THE PRIOR ART

U.S. Pat. No. 4,813,436 to J.C. Au describes a motion analysis system in which a video recording is made of a subject who is running or walking. Data from the video recording is processed along with signals from pressure sensitive insoles worn by the subject to permit analysis of the individual's gait.

U.S. Pat. No. 4,416,293 to Anderson et al describes a system in which a video monitor and camera are used to record the gait of an individual undergoing podiatric diagnosis and/or treatment.

U.S. Pat. No. 4,858,599 to Halpern describes a method and device for treating osteoporosis in which a platform is repeatedly raised and lowered to impart force to the bones of the subject on the platform.

U.S. Pat. No. 4,631,676 to Pugh describes a computerized video gait and motion analysis system.

U.S. Pat. No. 4,548,289 to Mechling describes a tilt-board for evaluation of balance reaction.

U.S. Pat. No. 4,375,674 to Thornton describes a combination three dimensional Kinesimeter and ergometer for determining reach, velocity, acceleration, and force generation at various positions.

U.S. Pat. No. 4,122,840 to Tsuchiya et al describes an apparatus for analyzing human balance in which load sensors detect load applied to foot steps and produce a signal display which is observed by the subject to induce adjustments in body load distribution to achieve balance.

PRIOR ART BIBLIOGRAPHY

Adelsburg, Stanley, PT; Pitman, Mark, MD; Alexander, Harold, PhD; "*Lower Extremity Fractures: Relationship to Reaction Time and Coordination Time*". Arch Physical Medicine Rehabilitation, Volume 70, October 1989, Page 737-739

Badke, MB; Duncan PW; "*Influence of Prior Knowledge on Automatic and Voluntary Postural Adjustments in Hemiplegic Subjects*". Supported by the Foundation for Physical Therapy. (Department of Physical Therapy, University of Wisconsin Hospital and Clinics, 600 Highland Avenue, Madison Wis. 53792) Page 789

Badke, Mary Beth; Duncan, Pamela W.; Di Fabio, Richard P.; "*Influence of Prior Knowledge on Automatic and Voluntary Postural Adjustments in Healthy and Hemiplegic Subjects*". Physical Therapy, Volume 67, October 1987, Page 1495-1500

Barin, Kamran; "*Human Postural Sway Responses to Translational Movements of the Support Surface*". Ninth Annual Conference of the Engineering in Medicine and Biology Society-*0745, 1987*

Bohannon, Richard W.; Smith, Melissa B.; Larkin, Patricia A.; "*Relationship Between Independent Sitting Balance and Side of Hemiparesis*". Physical Therapy, Volume 66, Number 6, June 1986, Page 944-945

Briggs, Randall C., Gossman, M.R., "*Balance Performance Among Noninstitutionalized Elderly Women*". Physical Therapy, Volume 69, September, 1989, Page 748-756

Crosbie, W. John, MSc; Nimmo, Myra A. PhD; Banks, Moira A., BA; "*Standing Balance Responses in Two Populations of Ederly Women: A Pilot Study*". Arch Physical Medicine Rehabilitation, Volume 70, October 1989, Page 751-754

Crowther, J.A., FRCS, "*Functional Anatomy of Balance*". Ear, Nose and Throat Journal ". Volume 63/November, 1984, Page 12

Dickstein, Ruth, Pillar, Thomas, "*Electromyographic Responses of Distal Ankle Musculature of Standing Hemiplegic Patients to Continuous Anterior-Posterior Perturbations During Imposed Weight Transfer over the Affected Leg*". Physical Therapy, Volume 69

Thorstensson, Alf; Oddsson, Lars; Carlson, Hans; Department of Physiology III, Stockholm, Sweden, "*Motor Control of Voluntary Trunk Movements in Standing*". Acta Physiol Scand 1985, 125, Pages 309–321

Winstein, C J , PhD, PT, Gardner, E.R., MS, PT, "*Standing Balance Training: Effect on Balance and Locomotion in Hemiparetic Adults*". Arch Physical Medicine Rehabilitation, Volume 70, October 1989, Page. 755–762

Wolf-Klein, Gisele P , MD, Silverstone, Felix A., MD, "*Prevention of Falls in the Elderly Population*". Arch Physical Medicine Rehabilitation, Volume 69, September 1988, Page 689–691

DETAILED DESCRIPTION OF THE INVENTION

Figure 1:
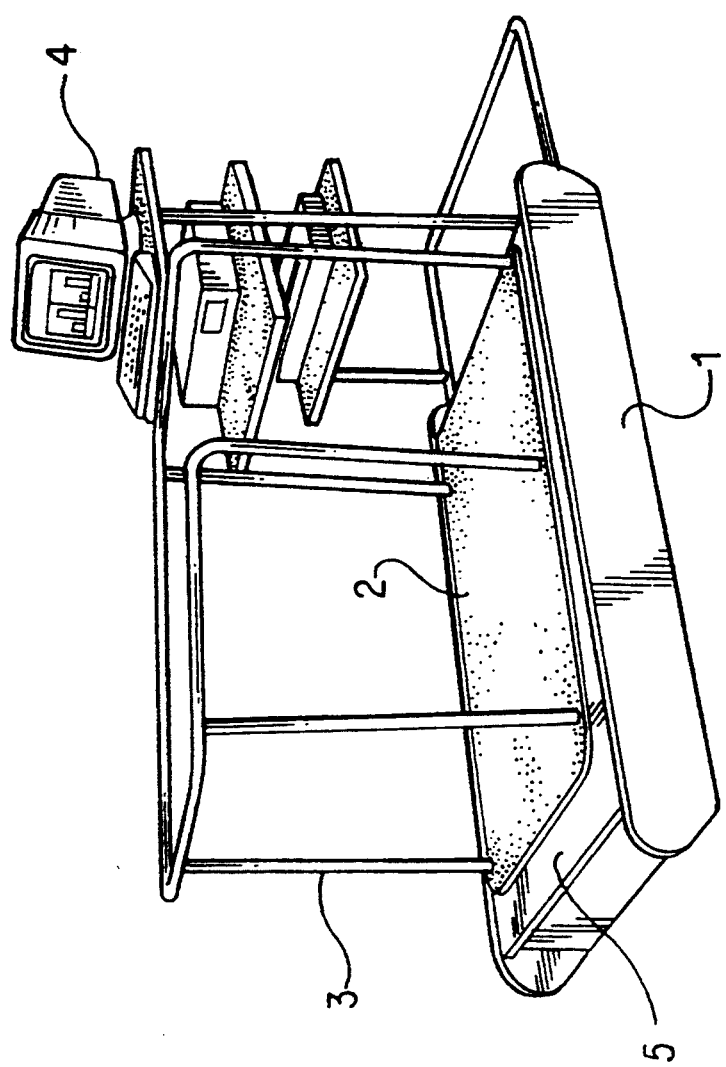
FIG. 1 is a side perspective view of the platform and control station of the invention.

The present invention uses a computer controlled motion system designed to quantitatively assess and then re-educate balance reaction, recovery time and motor control of human subjects. Testing and training can be performed in various postures, including standing, sitting, kneeling and quadruped positions. Both testing and training can be done in anterior-posterior, side-to-side, or diagonal directions. The platform can be programmed to move at various movement profiles in which the displacement, velocity and acceleration components of each test or training set are precisely controlled.

In one embodiment, the invention measures various reactions by timing foot movements. Numeric and graphic data presentations are displayed and stored to objectively document the patient's present dynamic performance. The appropriate training level can then be determined, practiced and stored as training programs to be retrieved during the next treatment. As equilibrium reactions and movement control improves, the training program can be modified to provide higher levels of task performance.

In accordance with the invention a device and method are provided for registering and evaluating the response of a human subject to induced imbalance. In a further embodiment, the present invention also provides a system and methodology for physical and rehabilitation therapy through a controlled exercise and motor response regimen.

In its essential elements, the present invention consists of a horizontal platform capable of accommodating a human subject in either a standing, seated, prone or quadruped position, which platform is adapted for controlled, linear displacement in a horizontal plane sufficient to induce imbalance in the subject.

Reaction to induced imbalance can be measured and recorded by means of pressure sensitive shoes worn by the subject which produce electrical signals as the subjects position and weight distribution shift in response to the induced imbalance. Various forms of pressure sensitive shoes or foot surfaces can be employed in accordance with the invention. Typically pressure sensitive switches are disposed in any array in the toe and heel portion of the sole or insole of a shoe or slipper to register changes in foot pressure as the individuals balance is disturbed and regained, as well as the interval involved. U.S. Pat. No. 4,745,930 to Confer and No. 4,503,705 to Polchaninoff both describe appropriate force sensors.

Reaction to displacement of the horizontal platform can also be monitored by other systems, which may present advantages if the individual is positioned on the platform in other than a standing position. Thus, in its other contemplated embodiments, the invention can include a chair or stool mounted on the platform for accommodating individuals in a seated position, a safety harness to prevent falls, and a raised platform to accommodate activity in the kneeling and quadruped positions.

The invention in its various embodiments will, however, be more fully appreciated by having references to the drawings.

FIG. 1 illustrates the more prominent external features of one embodiment of the invention. A platform, 5, capable of limited, controlled horizontal displacement is mounted on base 1, with a pad 2. Handrails are provided at 3 for security and the computer rack is disposed conveniently adjacent to the platform.

The Platform 5 moves linearly at a controlled speed, acceleration and distance. The movement is accomplished by a motor 14, shown in FIG. 2. The patient wears shoes attached with switches on the toes and the heels and stands on the platform. The platform is suddenly moved causing the person to lose his/her balance. The patient reacts to the movement and regains the balance. Losing and regaining of the balance is measured by monitoring the status of the foot switches.

Figure 2:
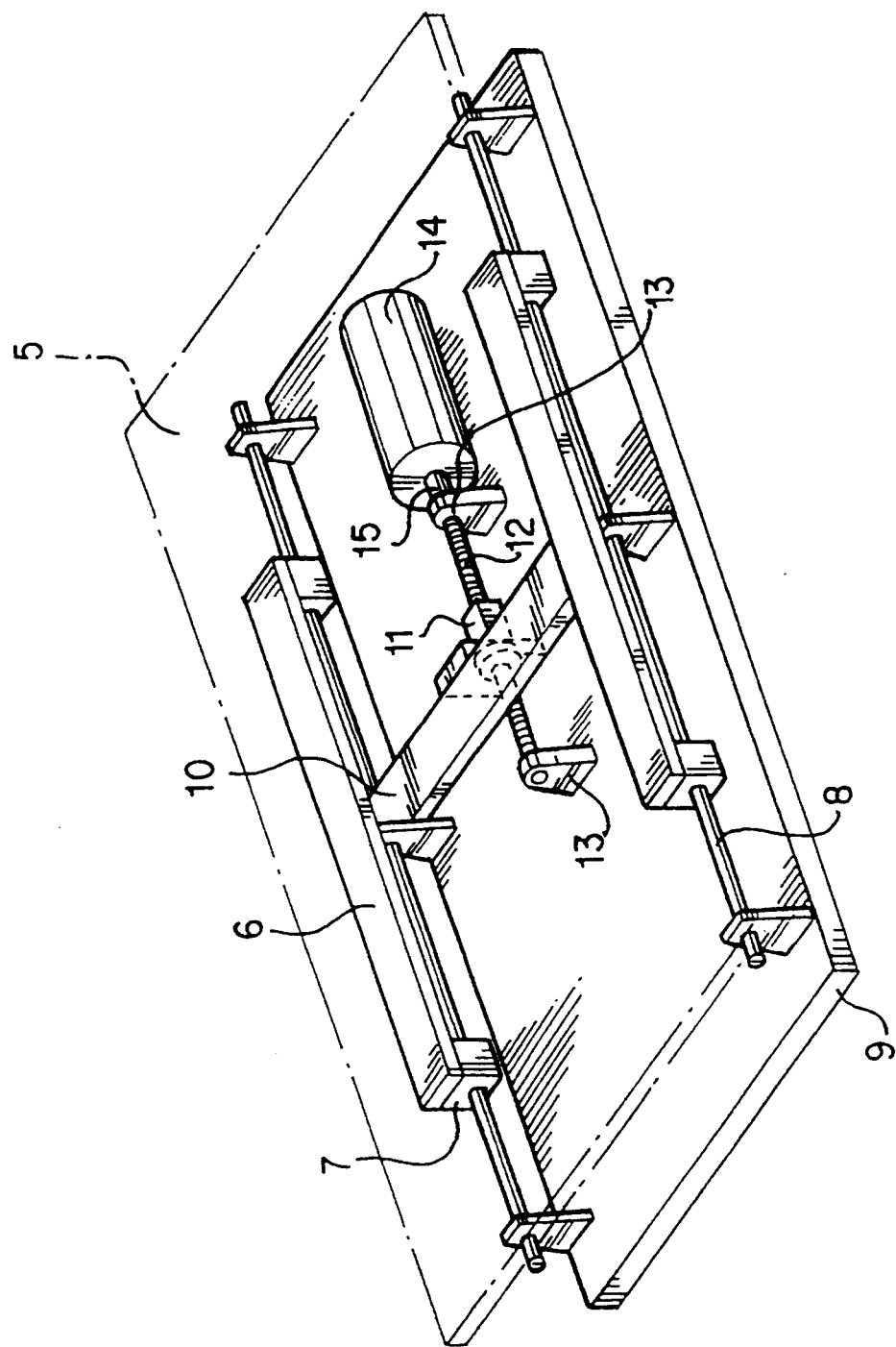
FIG. 2 is a perspective view of the underside platform activation mechanism of the invention.
Figure 3:
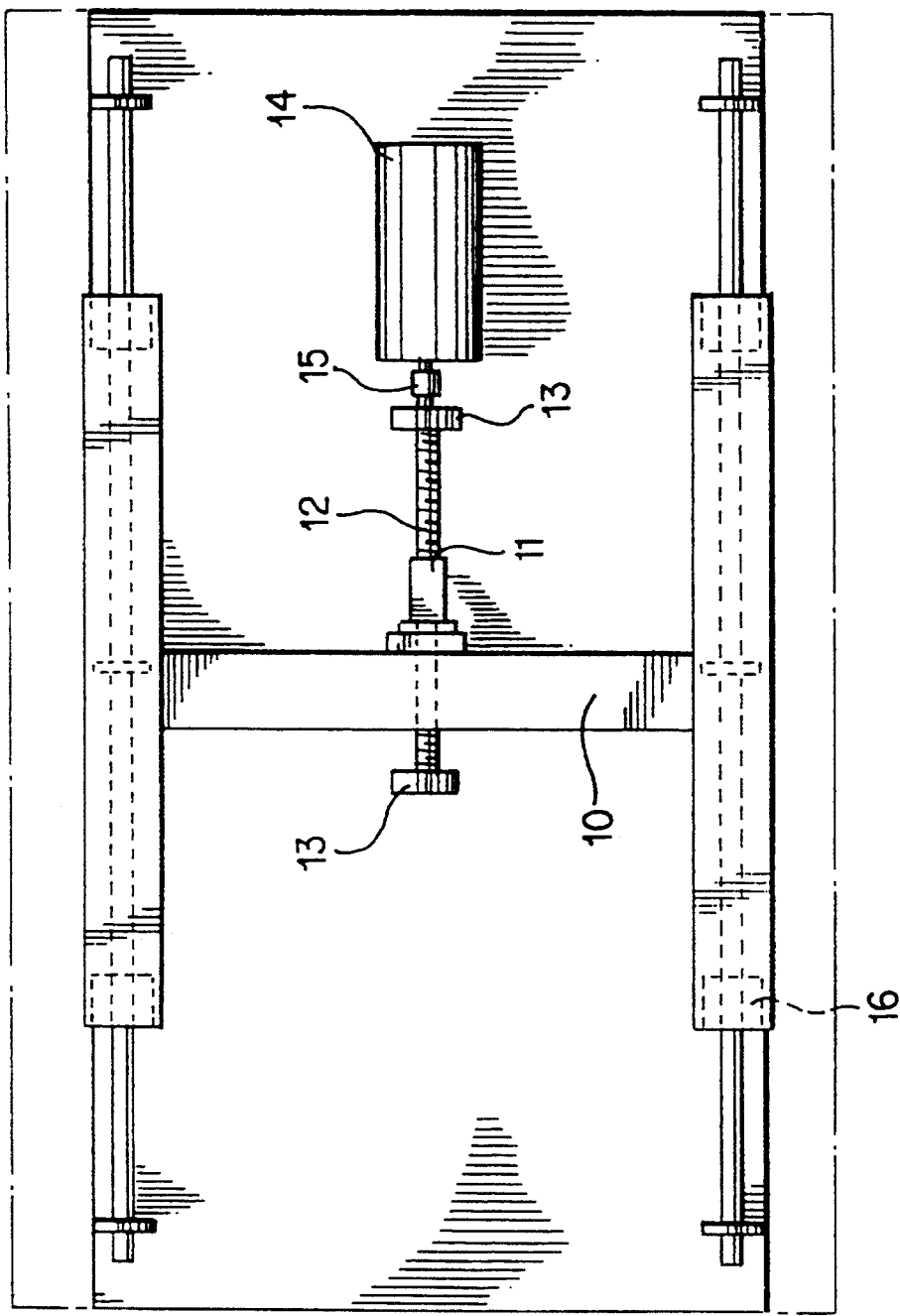
FIG. 3 is a top view of the underside platform activation mechanism.

As shown in FIGS. 2 and 3, the platform 5 is mounted on a H-shaped support frame 6. The side arms of the support frame are mounted on linear bearings 7 that move on two shafts 8 mounted on the machined base 9. The center cross piece 10 of the support frame is attached to a ball bearing nut 11 that moves on ball screw 12. The ball screw is mounted on two support bearings 13 and connected to the motor 14 through a flexible coupling 15.

Figure 4:
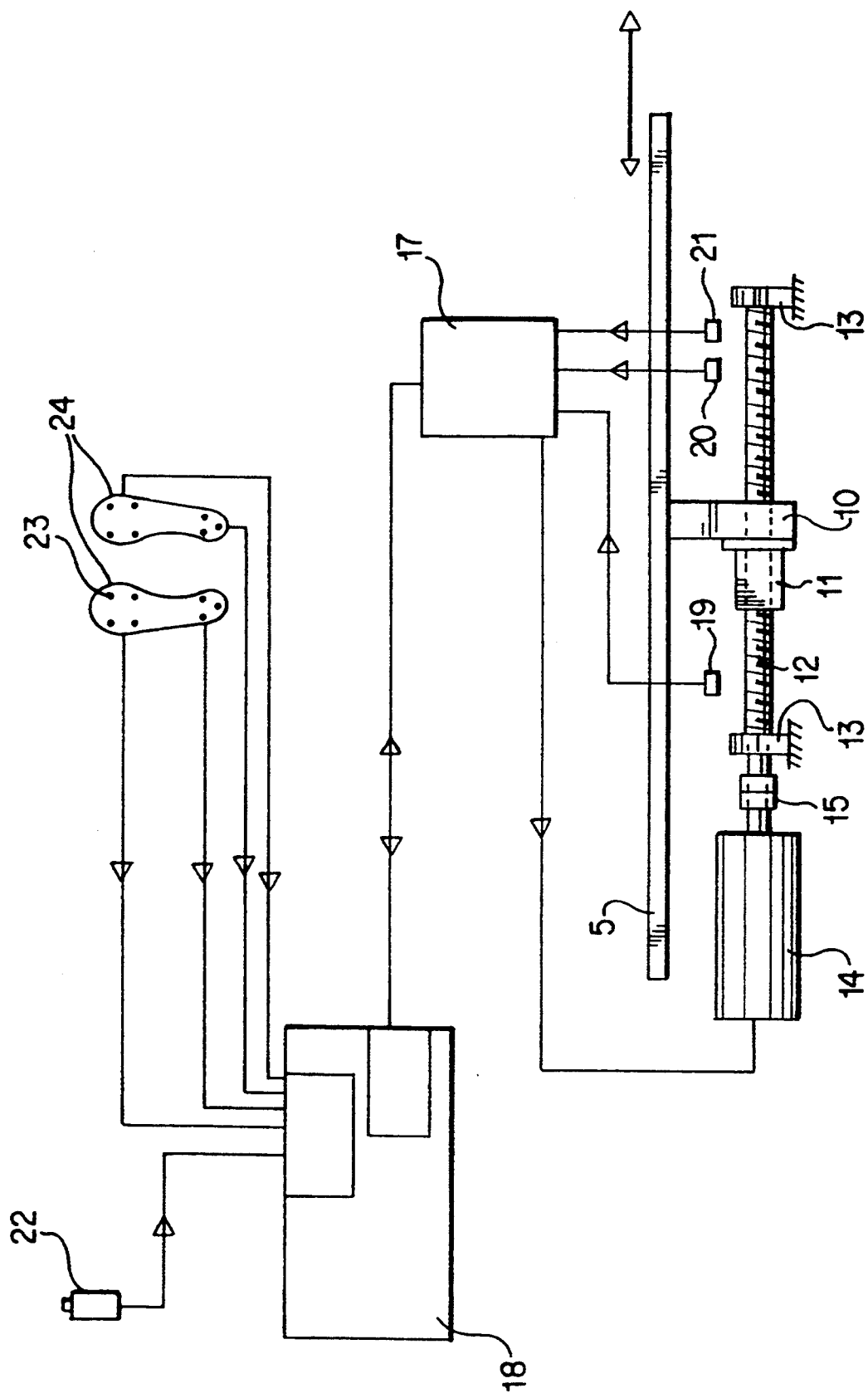
FIG. 4 is a schematic diagram illustrating connection of the active components of the invention.

When the motor is directed to turn, it rotates the ball screw with it, causing the ball bearing nut (and hence the platform) to move linearly. The speed, acceleration, direction and distance moved by the motor is controlled by a motion controller 17. As shown in FIG. 4, the motion controller receives its motion parameters (speed, direction, distance and acceleration) from the computer 18 through the serial port. There are three limit switches mounted on the base, which are triggered on as the platform passes by them. The switches are clockwise 19 and the counterclockwise limits 21 and the home switch 20. The two limit switches indicate the end of travel, and the home switch 20 is used to initialize (zero) the position of the motor. The three switches are input to the controller, which stops the motor in case a limit switch is found activated. The motion controller also sends information to the computer regarding the motion and limit switch status, when requested by it.

A remote switch 22 can be used in the system to start/stop motion during a test/exercise. It is connected to the computer through the parallel port and is monitored by the software. The foot switches 23 on the shoes 24 are connected to the parallel port of the computer, and thus monitored by the software.

Figure 5:
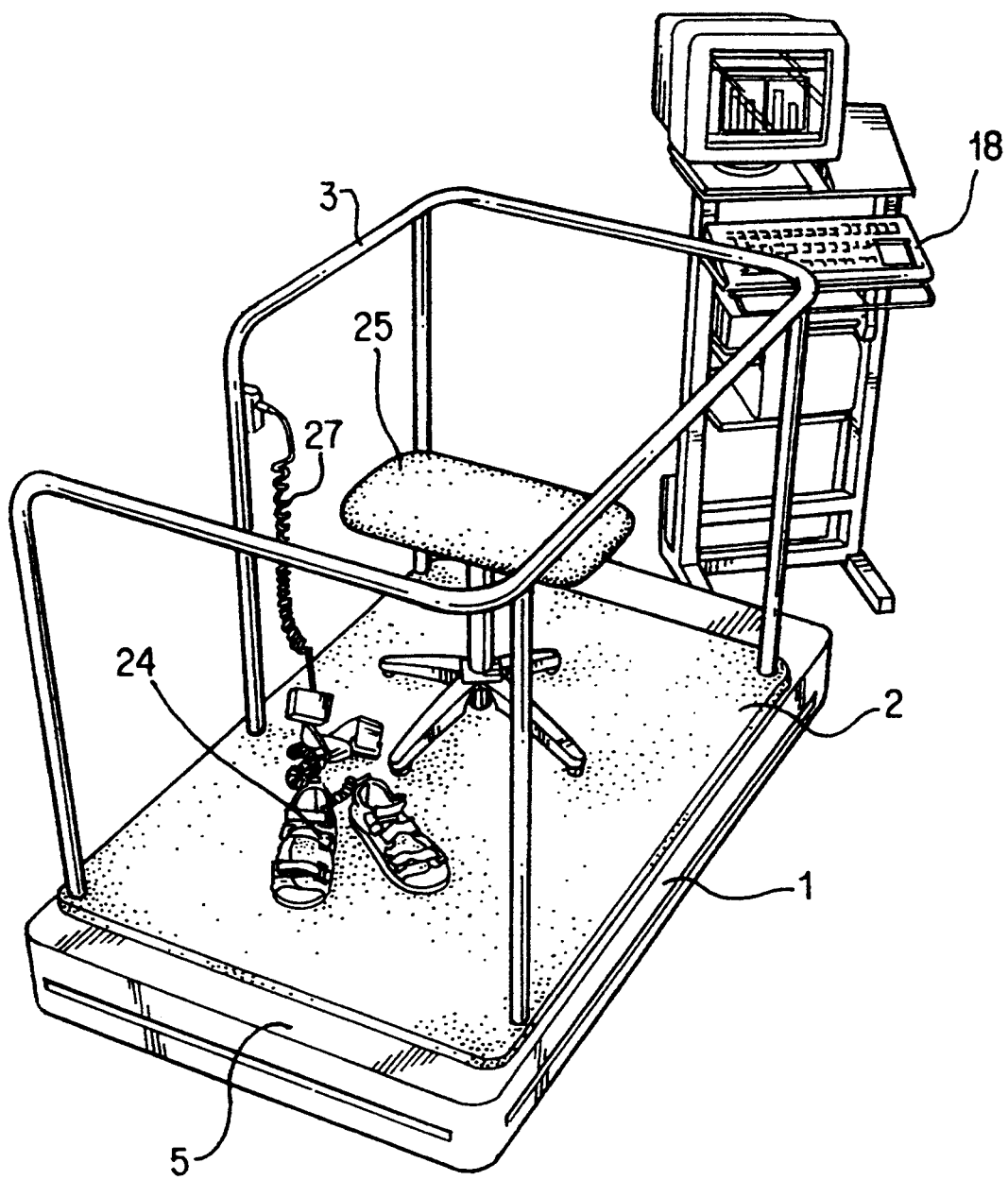
FIG. 5 is a perspective view of the invention including contact shoes, rails and stool.
Figure 6:
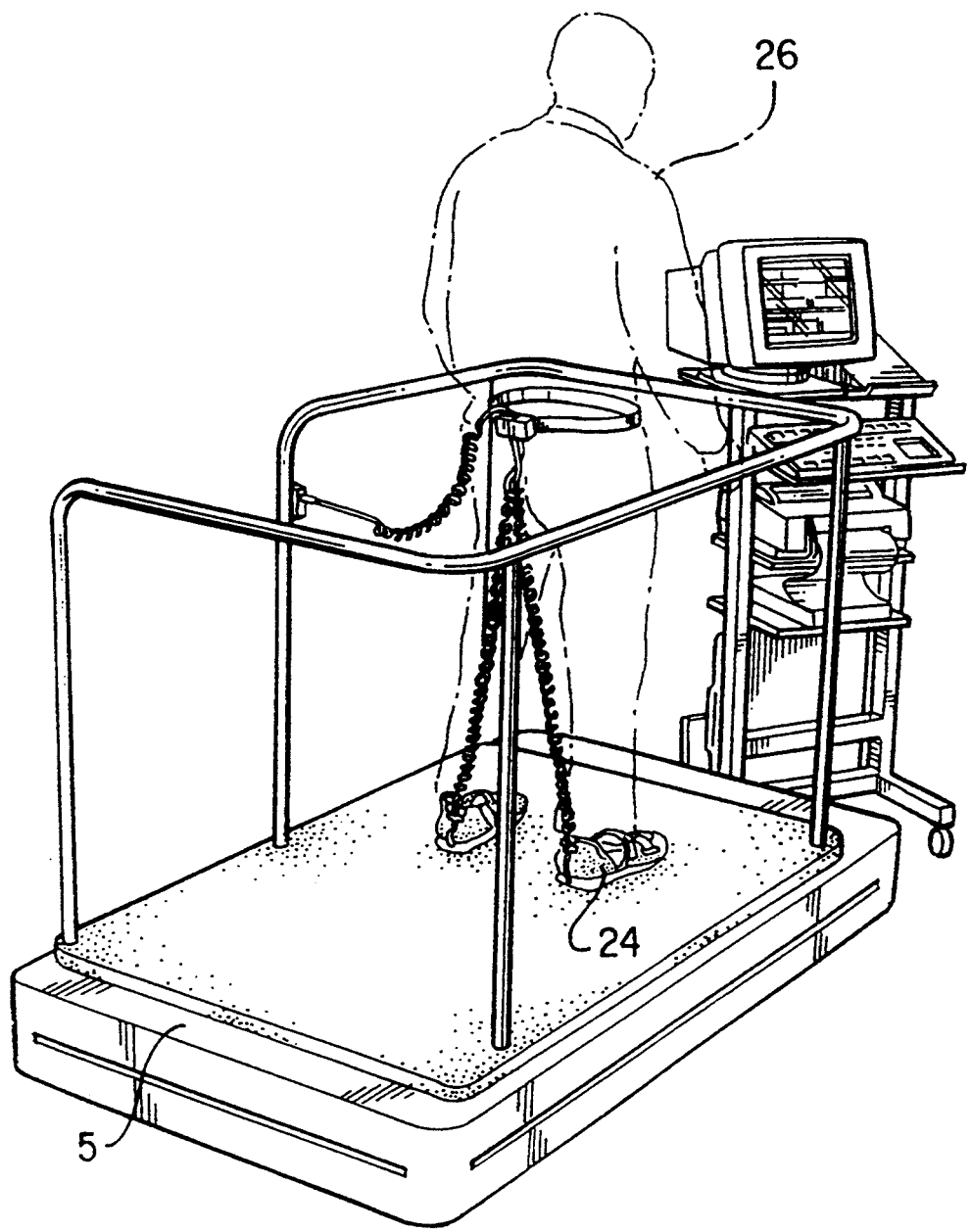
FIG. 6 is a perspective view showing an individual standing in the contact shoes in accordance with one mode of operation.

In FIG. 5 of the drawings, the contact shoes, 24, are shown connected by wiring; 27, through conduits in the railing, 3, to the computer control 18. FIG. 6 illustrates a subject, 26, standing on the platform 5 in shoes 24 in preparation for testing in accordance with the invention.

Figure 9:
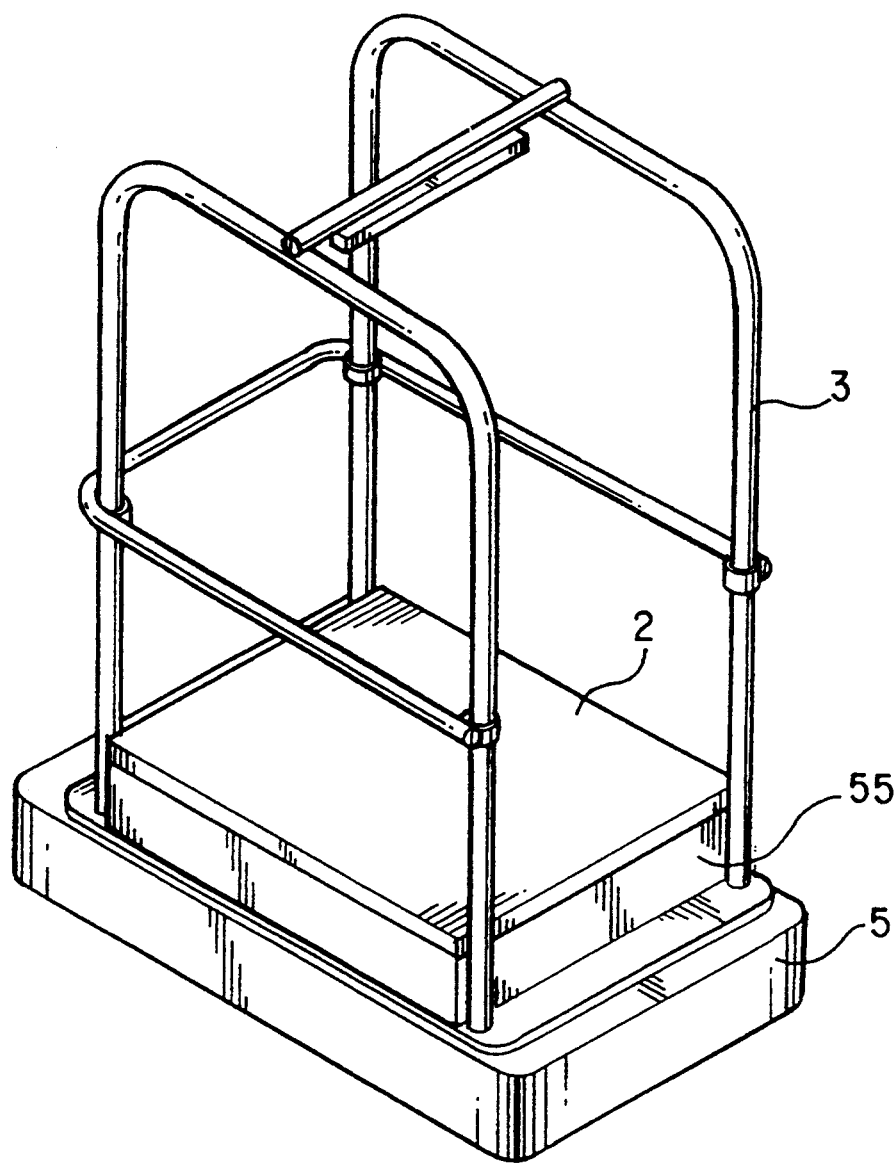
FIG. 9 is a perspective view of the platform of the invention with a pad and raised block.

Although not illustrated, a safety harness can be provided with the device to attach to the subject to prevent falling from any of the contemplated positions in an injurious manner. The safety harness can be attached to a bar that rotates 180° to allow the subject to be trained and tested anterior-posterior, side-to-side or in any of the four diagonal directions. Therapy in the kneeling or quadriped position with the assistance of an attendant is also facilitated by elevating the pad 2 by means of blocks or other raised structures interposed on the platform as shown in FIG. 9 of the drawings.

Figure 7:
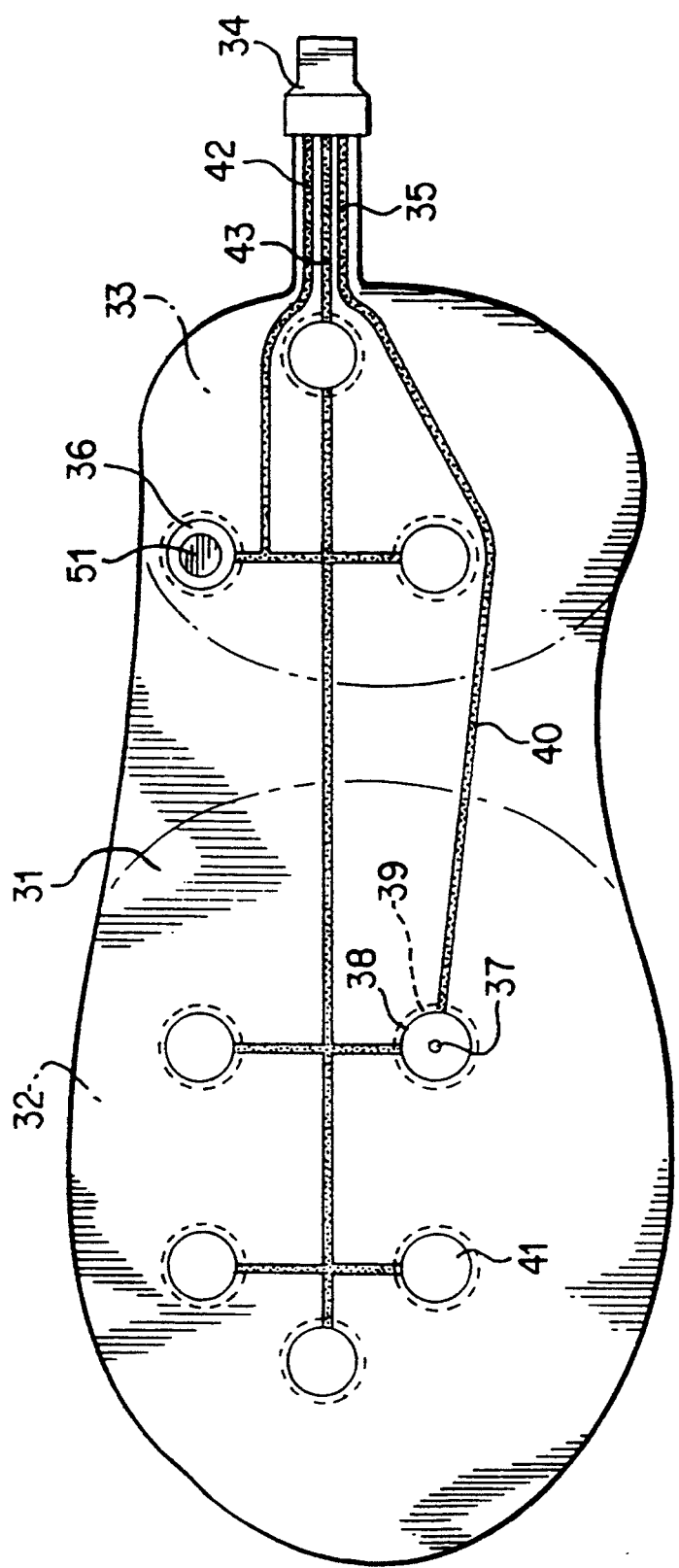
FIG. 7 is a top view of the contact shoe which can be used in accordance with the invention.
Figure 8:
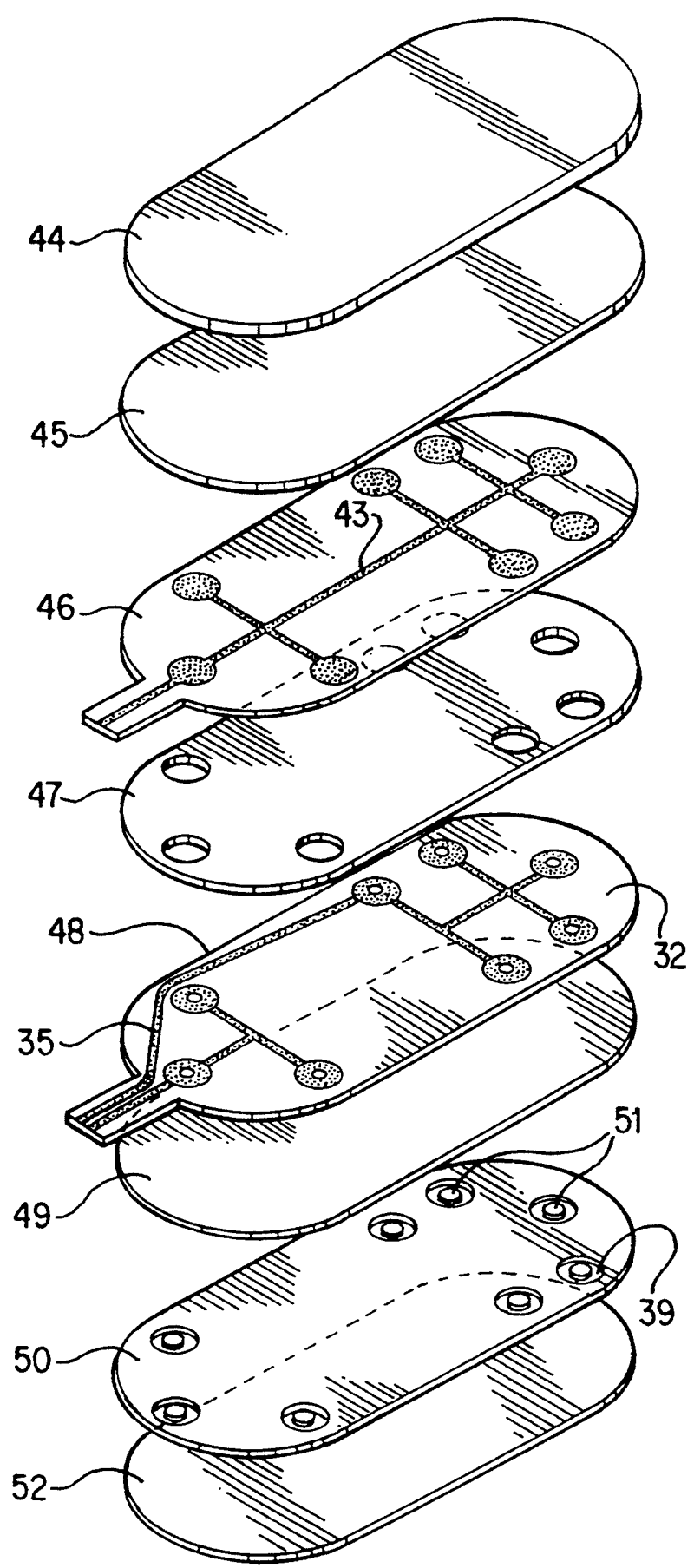
FIG. 8 is a perspective view showing the composite layers of the electric contact shoe.

A unique and preferred form of foot switch assembly is illustrated in FIG. 7 and 8 of the drawings. As shown in the drawings a composite, multilayer switch pad is provided which is adapted to be worn on the exterior side of the sole of the shoe or slipper in order to increase sensitivity to changes in foot pressure. FIG. 7 is a top view of the foot switch assembly 31, showing two groupings of switches in the heel area 33 and ball area 32 respectively. Three sensors 36 are provided in the heel area and five sensors 41, which can be formed from conductive ink, are provided in the ball area. The respective groups of sensors are connected in parallel circuits by means of conductive strips 40 so that if any one sensor in an area is activated, the entire area signals contact. The respective conductive strips are connected to leads 35, 42 and 43, which is a common ground, at the back of heel where a jack 34 is provided for connection to a monitor (not shown). Further details typically of the circuitry and structure of the individual switches used in the invention can be found in U.S. Pat. No. 4,745,930 to Confer, which is incorporate herein by reference.

FIG. 8 of the drawings illustrates the unique composite structure of the foot switch assembly which is positioned exterior to the sole of the shoe rather than interior to the sole or integrated within it as shown in U.S. Pat. No. 4,745,930. In the composite structure of FIG. 8, a spring steel plate 45 is provided between the shoe sole 44 and the switch assembly 46-48, which is generally similar to that of the Confer patent referred to above. This spring steel plate functions to provide rigidity to prevent deformation of the elastomeric members upon which foot pressure is exerted to close the sensor switches. A protective plastic layer is provided at 49 and spacer layer 50 has an array of cut out holes 39 to accommodate resilient pads or "bumpers" 51 which are located opposite sensor switches in the assembly 46-48. A final resilient layer 52 is provided on the exterior surface of the structure. Contact or release of contact is registered by pressure applied through layer 52 onto the pads 51. These pads then activate the respective switches in assembly 46-48 with which they are aligned. Greater sensitivity is thereby attained since foot pressure is applied directly to each individual switch rather than being dispersed through the sole of the shoe. As shown in FIG. 7 at 37 a non-conductive "dot" can advantageously be provided in the center of each sensor to provide a resilient release member to facilitate separation of the contact surfaces after pressure is relieved.

The present invention offers several options of testing, which are divided into testing for reaction time and testing for motor control. The various tests provide data on balance reaction and recovery time or motor control as determined by foot contact with the floor. Patient preparation for the test takes about 1 minute. The test itself requires 7 pre-test trials to familiarize the subject with the procedure. Actual data collection of 3 trials follows where the data is collected and stored in the computer under the subject personal file. A set of pre-tests and tests in the various directions usually requires 3–5 minutes.

The level of test difficulty can be chosen from pre-programmed motion descriptions. Challenging the subject's balance responses predominantly depends on the velocity and acceleration of the platform motion. There are multiple levels of difficulty that can be automatically selected although each of these can be modified to accommodate the individual patient needs. After completion of the appropriate tests the therapist selects the desired training program and the patient can train to improve his/her balance responses.

The purpose of the training program is to facilitate neuromuscular control of the individual body segments and the body as a whole. The computer controlled training session produces a repeated movement paradigm in order to continually challenge the static posture of the patient. In each training session, the subject is required to use the equilibrium and righting reactions and develop motor control.

Training of adults is usually done in standing and/or sitting postures. Movement direction can be set for forward/backward; side-to-side; or diagonal direction.

The pattern of platform motion can be selected from a list of pre-programmed training profiles. Each profile includes specific displacement, velocity, acceleration, and number of repetitions as well as locations and durations of pauses of platform motion. There are multiple pre-programmed, menu driven training sets of increasing difficulty. Each program can be easily modified by the therapist to meet the particular needs of each patient. The training program which is determined to be appropriate for the individual patient can be stored at the end of the session, as the patient individual file, and re-called automatically for the next session.

Pediatric patients can be trained not only in standing and sitting but also in kneeling, quadruped and even recumbent positions.

The invention is designed to improve upon presently available conventional treatment approaches to the deficient musculoskeletal and neurological patients. The addition of testing and training protocols enhances both the accuracy and efficiency of the patient's rehabilitation program. Precise testing of inadequate balance reactions (BR) or recovery time (RT) in various postures and different directions enables the therapist to quickly determine the appropriate training program. It may also help to identify the body segments which seem to adversely affect the normal responses and assist the therapist in focusing on musculoskeletal and/or neurological dysfunction.

Testing and training in the various postures can facilitate and enhance the rehabilitation process in a variety of clinical settings including hospitals, outpatient clinics, orthopedic and sports medicine clinics, rehabilitation centers and nursing homes.

Normatire reaction and recovery time data indicate symmetry between sides and between directions of responses. Thus any asymmetry of balance responses may indicate incomplete recovery of the neuromuscular system. Furthermore, healthy subjects have demonstrated the ability to respond to a fast movement profile by using only equilibrium reactions. Thus any subject that requires protective reactions, i.e. to change the support base, or can only perform the test at slow movement profiles is likely to have deficient neuromuscular performance.

The major cause for inappropriate responses may include musculoskeletal pain, disuse atrophy and peripheral as well as central nervous system damage.

The present invention provides a unique approach where the monitored variables are the actual segmental displacements, directly synchronized with platform movement. The collected data are of single dimension and are very easy to interpret. Furthermore, application of the sensors is very simple and unlike other balance units, requires very little time.

The invention is not limited to balance training in the standing posture. Many patients may present balance and neuromuscular deficiencies in other postures, such as sitting. The invention can train in the sitting and quadruped position and thus offer more comprehensive management of the aforementioned dysfunctions.

The invention challenges the patient's subconscious reaction to the abrupt yet controlled dispositions of the platform and thus minimizes the dependence of the monitored variables on the volitional, cortically controlled balance adjustments which are typical during training on other balance systems. The more advance subcortical automatic sensory-motor integration offered by the invention closely simulates the real, functional requirements for neuromuscular balance responses.

In addition, to assessing balance reaction, the present invention can be used to assess motor control. Many traumatic or disease related musculoskeletal and neurological disorders not only present as deficiencies in equilibrium and supportive reactions, but also as inadequate total body and/or segmental sensorimotor control. Motor control testing provides the opportunity to measure a subject's motor abilities and sensorimotor skills while performing a particular task on either a stationary or moving platform. These tasks include single limb stance, stepping, and heel-toe transitions. Additional information is also gained from the performance of these tests; i.e. cadence, swing/stance ratios, and heel/toe ratios.

While motor control tests can be performed on a stationary platform, a moving platform increases the level of test difficulty. When platform motion is involved, the motion is continuous in both directions (forward and backward). The motion descriptions described above in balance testing are also used in the motor control testing. One of five standardized motion description can be modified to accommodate to the individual's abilities.

In motor control testing, there are three different standard tests. The three tests are single limb support, stepping, and heel-toe transition.

In the single limb support the subject is asked to raise one foot from the platform surface and maintain that one-legged stance for five seconds. This test can be viewed as preparation for the stance phase of gait. It should be performed for the right and left lower extremities, beginning with the uninvolved extremity when applicable. The results are reported in terms of swing and stance times (in milliseconds) for each extremity. Then, in comparing right to left, a deficit can be seen.

Rapid stepping is likened to running in place for five seconds. The instruction to the subject is to step in place as quickly as possible until told to stop. This test can be viewed as preparation for walking and running. Test results are reported in terms of swing and stance bilaterally (in milliseconds), swing/stance percentages for each extremity, and cadence (steps per minute). Difficulty in shifting weight from side to side can be seen. Other information gained from this test includes movement coordination of the trunk, pelvis, and lower extremities and consistency of effort (since the graphic display shows each swing and stance bilaterally, each phase can be studied over time and should be consistent).

Heel-toe transition involves the subject rocking back and forth from the heels to the toes. The subject is asked to do this as quickly as possible until told to stop. This test can be viewed as preparation for sports activities, in particular. This should be done bilaterally, followed optionally by single limb transitions. When performed singularly, begin with the uninvolved extremity. Here, results are reported in terms of the number of heel-toe transitions performed in a five second period of time, and the average contact time of the heel and toe for each extremity in milliseconds and as a percentage. This test can be useful in the area of orthopaedics as particularly knee and ankle deficits can be reflected in the performance of heel-toe transitions.

What is claimed is:

1. A device for registering and evaluating the response of a human subject to induced imbalance comprising a horizontal platform means for accommodating said human subject; said platform means being adapted for controlled linear displacement in a horizontal plane to cause said induced imbalance and comprising a horizontal surface mounted on linear bearings which engage rails and connected to a motor through means for translating rotation of the motor into linear motion to cause said displacement at a controlled speed and acceleration and for controlled duration and distance; means for detecting said imbalance and the response of said subject thereto and for producing signals which characterize said imbalance and response; means for transmitting said signals to evaluation, display and recording means for registering and evaluating said imbalance and response thereto by said subject.

2. The device of claim 1 wherein said controlled, linear displacement of said platform is at controlled speed, acceleration and for controlled duration and distance.

3. The device of claim 1 wherein said platform is provided with limit switch means to limit said displacement of the platform means and to cause said motor and means for translating to returns said platform means to its initial position subsequent to said displacement.

4. The device of claim 1 in which elevation means are provided to raise the height of said platform means.

* * * * *